United States Patent [19]
Wieder et al.

[11] 4,432,907
[45] Feb. 21, 1984

[54] DIAMINE ACID FLUORESCENT CHELATES

[75] Inventors: Irwin Wieder; Robert H. Wollenberg, both of Los Altos, Calif.

[73] Assignee: Analytical Radiation Corporation, Los Altos, Calif.

[21] Appl. No.: 260,574

[22] Filed: May 5, 1981

Related U.S. Application Data

[62] Division of Ser. No. 73,728, Sep. 10, 1979, Pat. No. 4,352,751.

[51] Int. Cl.³ .................. C07C 101/26; C07C 103/18; C12Q 1/06; G01N 33/52; G01N 33/74; G01N 33/76; G01N 33/78; G01N 33/92; G01N 2/38
[52] U.S. Cl. ................................. 260/429.2; 424/7.1; 252/301.16; 252/301.17; 252/301.18; 260/429 J; 260/429.1; 260/112 R; 260/112.5 R; 260/113; 260/112 T; 260/112.7; 260/124 R; 560/169; 562/448; 562/507; 562/565; 562/566; 435/4; 435/7; 436/500; 436/501; 436/503; 436/543; 436/546; 436/513; 436/56; 436/172; 436/547; 436/537
[58] Field of Search ...................... 252/301.16, 301.17, 252/301.18; 260/429.2, 429 J, 429.1, 112 R, 112.5 R, 113, 112 T, 112.7; 424/124 R, 7.1; 560/169; 562/448, 507, 565, 566; 250/453, 461 R, 461 B, 459; 435/4, 7; 436/500, 537, 501, 547, 503, 513, 543, 545, 56, 172

[56] References Cited

U.S. PATENT DOCUMENTS

| | | | |
|---|---|---|---|
| 2,413,856 | 1/1947 | Bersworth | 560/169 |
| 2,428,353 | 10/1947 | Bersworth | 560/169 |
| 2,530,147 | 11/1950 | Bersworth | 560/169 |
| 2,680,094 | 6/1954 | Bartlett et al. | 560/169 |
| 2,802,868 | 8/1957 | Schlapfer et al. | 562/448 |
| 3,024,277 | 3/1962 | Hotten | 560/169 |
| 3,278,392 | 10/1966 | Patchornik et al. | 435/4 |
| 3,351,658 | 11/1967 | Bersworth | 560/169 |
| 3,429,915 | 2/1969 | Bersworth | 560/169 |
| 3,450,753 | 6/1969 | Bersworth | 560/169 |
| 3,497,535 | 2/1970 | Lennon | 560/169 |
| 3,580,950 | 5/1971 | Bersworth | 560/169 |
| 3,660,388 | 5/1972 | Dazzi et al. | 260/246 B |
| 3,787,482 | 1/1974 | Bersworth | 560/169 |
| 3,873,514 | 3/1975 | Chu et al. | 106/208 |
| 4,058,732 | 11/1977 | Wieder | 250/461 B |
| 4,150,295 | 4/1979 | Wieder | 250/461 B |
| 4,352,751 | 10/1982 | Wieder et al. | 424/1.5 |
| 4,374,120 | 2/1983 | Soini et al. | 436/546 |

FOREIGN PATENT DOCUMENTS 7920798 9/1980 Sweden.
79055453 12/1980 Sweden.
81207534 9/1982 Sweden.

OTHER PUBLICATIONS

Brund, A. J., et al., JACS, vol. 78, pp. 2723-2728 (1956).
C. A., vol. 92, 106582f (1980).
Charles, R. G., et al., J. Inorg. Nucl. Chem., vol. 28, pp. 527-536 (1966).
Heller, A., et al., J. Chem. Phys., vol. 42, No. 3, pp. 949-955 (1965).
Spedding, F. H. et al., JACS, vol. 78, No. 1, pp. 34-37 (1956).
Moeller, T., et al., J. Inorg. Nucl. Chem., vol. 20, pp. 261-273 (1961).
Krejcarek, G. E., et al.; Biochem. Biophys. Res. Comm., vol. 77, No. 2, pp. 581-585 (1977).
Khaw, B., et al., Science, vol. 209, pp. 295-297 (Jul. 1980).
Sundberg, M. W., et al., Nature, vol. 250, pp. 587-588 (1974).
Leung, C. S. H., et al., Biochem. Biophys. Res. Comm., vol. 75, pp. 149-155 (1977).

*Primary Examiner*—Teddy S. Gron
*Attorney, Agent, or Firm*—Burns, Doane, Swecker & Mathis

[57] ABSTRACT

Species-linked diamine triacetic acids of the formula

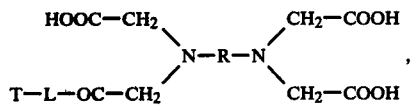

wherein T is an organic species containing at least one amine, hydroxyl, or thio functional group, L is the residue of at least one of those functional groups and R is a two or more atom long covalent bridge, are disclosed. Methods for their preparation, for the preparation of metal chelates from them and for the use of the chelates are also disclosed. In a preferred embodiment, the metal ions employed in the formation of the chelates are rare earth metal ions capable of forming fluorescent chelates which can in turn be employed in fluoroassay techniques.

30 Claims, No Drawings

DIAMINE ACID FLUORESCENT CHELATES

This is a division of application Ser. No. 73,728, filed Sept. 10, 1979, now U.S. Pat. No. 4,352,751.

FIELD OF THE INVENTION

The subject of this invention is a diamine triacetic acid capable of forming metal chelates. More particularly, this invention relates to a bifunctional ligand useful to bind metal ions to organic species such as organic target molecules or antibodies, preferably to form species-linked fluorescent rare earth metal chelates useful in fluorescent assay techniques.

BACKGROUND OF THE INVENTION

Fluorescence techniques are finding increasing application in chemical and biochemical and medical analyses. Fluorescence measurement methods are intrinsically extremely sensitive. They can offer at least the sensitivity of radiochemical methods without the hazards associated with radiation.

U.S. Pat. Nos. 4,150,295 and 4,058,732, issued on Apr. 17, 1979 and Nov. 15, 1977, respectively, and a chapter appearing at pages 67–80 of *Immunofluorescence and Related Staining Techniques*, Knapp, et al eds. (1978, Elsevier/North Holland Biomedical Press) disclose the general concept of fluorescently quantitating nonfluorescent species using fluorophores with long decay lifetimes in comparison with ambient fluorescence. In this method, an atomic scale fluorescent tag (fluorophore) is chemically covalently affixed to the individual molecules of a species. This species may be an organic target molecule itself or it may be a molecule essentially identical with a target molecule or it may be an antibody specific to a target molecule. After suitable procedures, dependent on the form of the assay, the tagged species are excited and, using time-gated techniques taught in the three references, their fluorescence measured. Using the magnitude of the observed fluorescence and a previously prepared fluorescence/concentration standard curve, the amount of target is determined.

Fluorophores and tagged species useful in such a determination ideally have a long fluorescent decay lifetime and retain their ability to fluoresce throughout the period of the analysis. For sensitive assays it is also important that the fluorophore and its linkage to other species be stable even at very low concentrations such as in the range of nanograms/cc and lower such as even to femtograms/cc. For many immunoassays it is desirable that the fluorophore be water soluble so as to be reacted with antibodies in an environment which preserves immune reactivity.

The metal chelates of the present invention include within their number a family of species-bound ligands which possess all of these desired properties. In addition, they are simple and inexpensive to prepare.

STATEMENT OF THE INVENTION

Stated in its broadest sense, our invention is that an organic species (herein denominated as "T") having at least one of the functional groups

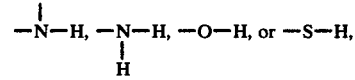

can be attached to one, and essentially only one, of the four carboxyl groups of diamine tetraacetic acids forming a stable structure possessing the configuration as shown in General Formula I wherein R is a two or more atom long covalent bridge and L is the deprotonated equivalent of said functional group on the species molecule, T.

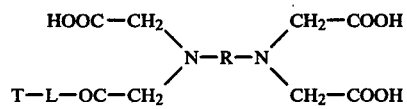

Since T may contain more than one L group, more than one diamine triacetic acid may be so covalently linked within this formula.

These covalently linked products (Formula I.) are referred to as "species-linked diamine triacids". They form stable chelates with various metal ions. These chelated complexes (Formula II.) constitute another aspect of this invention

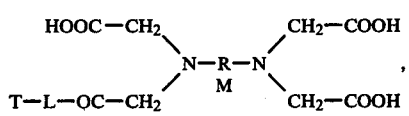

wherein "M" is a metal ion capable of forming a coordination complex with diamine tri- or tetraacids. In a preferred embodiment, the metal ion, M, is an ion of a rare earth metal capable of forming a fluorescent chelate complex.

In a third aspect of this invention, a particularly favorable complex is formed when an activator such as a salicylic acid is also present in a ternary complex combination with the rare earth metal ion and the species-linked diamine triacid.

In a fourth aspect, this invention provides a process for determining the concentration or presence of an organic species, T, such as a target molecule or an antibody that contains at least one of the groups

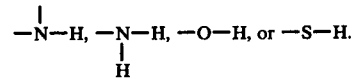

The process involves contacting such a species molecule with a substantial excess of a diamine tetraacetic acid dianhydride of General Formula III, wherein R is a two or more atom long covalent bridge,

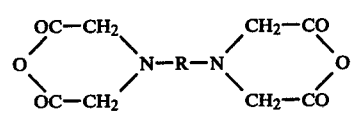

under conditions to effect reaction of at least one of said groups on the species molecule with one of the anhydride groups of the dianhydride to yield a species-bound diamine triacid anhydride; hydrolyzing the remaining anhydride group to yield the species-linked diamine triacid; admixing said species-linked diamine triacid in solution with a rare earth metal ion to form a species-linked rare earth chelate; then, optionally after suitable procedures depending on the type of assay involved, flooding this species-linked rare earth chelate with an activator such as a salicylic acid; measuring the intensity of fluorescence of said fluorescent complex; and relating the intensity of the observed fluorescence to the intensity of fluorescence of a known concentration of such a fluorescent complex.

In a fifth aspect, this invention provides a process for detecting the presence or amount of a target molecule by coupling one or more tetraacid dianhydride molecules of Formula III to

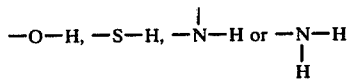

sites on an antibody specific to a target molecule to form an antibody with one or more diamine triacid molecules covalently linked thereto; forming a rare earth chelate of said antibody coupled triacid; exposing a quantity of the coupled antibody to tissue, liquid, or solid substrate suspected of containing the target molecule to bind said target to the antibody, removing excess unbound antibody, flooding the liquid, tissue, or solid substrate with a fluorescent activator specific to the rare earth triacid chelate and measuring or detecting the fluorescence as an indicator of the quantity or presence of said target molecules.

DETAILED DESCRIPTION OF THE INVENTION

This Description will be divided into the following sections:
The Species-Linked Diamine Triacid Compounds,
Metal Complexes,
Ternary Combinations with Flooders,
Preparative Methods,
Species Molecules, and
Analysis Techniques.

THE SPECIES-LINKED DIAMINE TRIACID COMPOUNDS

These compounds have the structure set forth in General Formula I. In Formula I, R is a two or more atom covalent bridge. The two or more atoms refer to the atom in the bridge itself. They may be substituted with additional atoms or groups if desired. The function of R is to covalently bond together the two amine diacetic acid groups in a spacing which permits the two amine diacetic acid groups to form a stable chelate with metal ions. Thus, any group that will serve this function without interfering with the chelate-forming ability of the amine diacetic acid groups can be employed as R.

Preferably, R is an optionally substituted two to eight atom covalent bridge selected from carbon-oxygen ether bridges, carbon-nitrogen polyalkyl secondary or tertiary amide bridges and carbon-carbon bridges including alkylenes, cycloalkylenes, or arylenes, all either unsubstituted or containing substituents pendant from the bridge. Substituents include, for example, alkyls of from one to about ten carbon atoms, aryls of from six to ten carbon atoms, aralkyls and alkaryls of from seven to about fourteen carbon atoms. The bridges or the aforementioned substituents may also be substituted with carboxyls, carbonyls, ethers, carbamates, secondary amides, sulfonates, sulfamates, and the like. Exemplary R groups include ethylene, n-propylene, isopropylene, the various butylenes including n-butylene, 1- and 2-methylpropylene, 1-propylethylene, 1-cyclohexylethylene, 1-phenylethylene, alkyl-substituted 1-phenylethylenes and propylenes, 1-benzylethylene, 2-amidopropylene, cyclohexyl-1,2-ene, phenyl-1,3-ene, the diethylene-ether —CH$_2$—CH$_2$—O—CH$_2$—CH$_2$—, the triethylene diether —CH$_2$—CH$_2$—O—CH$_2$—CH$_2$—O—CH$_2$—CH$_2$—, and the like. This list is not intended to be inclusive but merely to represent typical embodiments of group R.

For reasons of simplicity of preparation, unsubstituted alkylenes of from two to five and preferably two to four carbons in length are preferred R's with ethylene and propylene being more preferred and ethylene being the most preferred R.

The species-linked diamine triacid compounds of this invention contain one or more functionalities, L, which are a primary or secondary amide nitrogen, an ester oxygen or a thioester sulfur. Each unit of L serves as a covalent linkbetween one unit of the diamine ligand and the species molecule, T. The choice of L depends upon the nature of the species molecule as L may be derived from an amine (primary or secondary), a hydroxyl or a thiol present on the species molecule. In general, the amide nitrogens are the preferred L groups with the amide group (thus derived from a primary amine group on T) being the most preferred.

The species-linked diamine triacid compounds of the invention contain two amine groups, one of which carries two acetic acid groups and the other of which carries one acetic acid group and one acetic acid/L-T adduct. For purposes of simplicity, the three acetic acid groups are depicted in their protonated form throughout this specification and claims. It will be appreciated that in actuality these groups, being weak acids, exist in equilibrium between the protonated form shown and the corresponding deprotonated salt form, —COO$^-$. The exact proportions of the two forms depend upon the pH and composition of the environment of use. It is intended that the protonated form shown shall represent the equilibrium of the two forms which actually exists.

METAL COMPLEXES

The species-linked diamine triacids of this invention are effective chelating ligands. It appears that their complex-forming ability is similar if not essentially the same as that of the corresponding non-species-linked diamine tetraacetic acid ligands (such as ethylenediamine tetraacetic acid - EDTA). It further appears that the fourth carbonyl group, although used in the attachment to the species, may be able to function as a point of coordination with metal ions and thus that the dissociation constants of complexes formed with the diamine triacids of this invention are very similar to those obtained with the diamine tetraacetic acids of the art.

The metal ions, M, which can be complexed include ions of radionucleotides as well as nonradioactive metal ions. Although not extensively proven, it appears that essentially all of the art-known complexes of metal ions with EDTA and its non-species-linked analogs can be prepared using the species-linked ligands of this invention. For example, complexes can be formed with M equal to ions of the transition metals as well as the rare earth metals of both the actinide and lanthanide series. Exemplary metal ions represented by M include $Al^{+++}$, $Am^{+++}$, $Cd^{++}$, $Ce^{+++}$, $Cf^{+++}$, $Cm^{+++}$, $Co^{++}$, $Co^{+++}$, $Cr^{++}$, $Cr^{+++}$, $Cu^{++}$, $Dy^{+++}$, $Er^{+++}$, $Eu^{+++}$, $Fe^{++}$, $Fe^{+++}$, $Ga^{+++}$, $Gd^{+++}$, $Hg^{++}$, $Ho^{+++}$, $In^{+++}$, $La^{+++}$, $Lu^{+++}$, $Mn^{++}$, $Mn^{+++}$, $Nd^{+++}$, $Ni^{++}$, $Pb^{++}$, $Pd^{++}$, $Pm^{+++}$, $Pr^{+++}$, $Pu^{+++}$, $Pu^{++++}$, $Sb^{+++}$, $Sc^{+++}$, $Sm^{+++}$, $Sm^{++}$, $Sn^{++}$, $Tb^{+++}$, $Th^{++++}$, $Ti^{+++}$, $Tl^{+++}$, $Tm^{+++}$, $V^{+++}$, $V^{+++++}$, $VO_2^+$, $Y^{+++}$, $Yb^{+++}$, $Zn^{++}$, and $Zr^{++++}$.

Because of the scope of the possible metal ions to be incorporated and the wide range and diversity of properties that such metal ions exhibit, the metal ion complexes in accordance with this invention find application and utility throughout the field of chemical analysis. The presence of the metal ions linked by the present invention to the species molecule can be detected by such techniques as radioassay, X-ray scattering or fluorescence, NMR or ESR shifts, or the like, depending upon the metal ion incorporated. In a preferred embodiment, the metal ions employed are those rare earth metal ions which form complexes with EDTA type chelating ligands. Preferred among these are terbium, dysprosium, europium, samarium, and neodimium with terbium and europium being more preferred and terbium being the most preferred rare earth for forming metal ion M.

The complexes formed between the metal ion, M, and the species-linked diamine triacid is considered to be a 1:1 equimolar metal:chelate complex. It is represented structurally by the structure given as General Formula II.

TERNARY COMBINATIONS WITH FLOODERS

The preferred application of the species-linked diamine triacids of this invention is to employ them as chelating ligands in fluorescent rare earth metal complexes. The utility of these complexes in fluorescence analytical techniques has been found to be substantially enhanced when a third component is present in the complex. This third component, a promoter, is generically referred to as a "flooder" because it is usually added in large excess. Flooders, which are also referred to as promoters or sensitizers, increase the fluorescence excitation efficiency of the rare earth chelates and have been disclosed in non-species-linked rare earth ions and chelates. See Dagnall et al, ANALYST, 92, 358–363, (1967); Heller and Wasserman, J. CHEM. PHYS., 42, 949–955, (1965); McCarthy and Winefordner, ANAL. CHEM., 38, 848, (1966); Taketatsu et al, TALANTA, 13, 1081–1087, (1966); Alberti et al, ANAL. CHEM., 38, 214–216, (1966) and Charles et al, J. INORG. NUCL. CHEM., 28, 527–536, (1966). These references and their disclosure of useful flooders are incorporated herein by reference. This is not intended as a complete list but is suggestive of the large number of flooding agents that can be used with the species-linked diamine triacids of this invention.

Many of these flooders appear to have coordination properties and to act by occupying sites on the rare earth metal ion that are not already occupied by the species-linked diamine triacid ligand. In so doing, they become closely coupled with the metal ion allowing for efficient energy transfer from the flooder to the rare earth metal.

Examples of complex-forming flooders are 5-sulfosalicylic acid (5-SSA), 4-aminosalicylic acid, salicylic acid, other substituted salicylic acids, dipicolinic acid, and the like. These materials are especially useful with terbium complexes, which application demonstrates their action.

A complex of a species-linked diamine triacid and terbium exhibits an excitation band near 2400 Å. This is a relatively weak band and, at this wave length, is not at a convenient part of the spectrum. When 5-SSA is added as a flooder a strong excitation band is observed in the near ultraviolet, near 3100 Å, a much more convenient wavelength from the standpoint of sample transmission.

Examples of flooders especially useful with europium include salts, such as potassium carbonate, sodium tungstate, and the like, and organic materials such as phenanthroline.

Except in cases where the concentration of species-linked diamine triacid is high, such as $10^{-1}$ to $10^{-4}$ M, in which case flooder concentration will be similar, the amount of flooder used is very large relative to the amount of species-linked diamine triacid. It is generally preferred to use at least $10^3$ times as much flooder as metal ion or diamine triacid, on a molar basis with molar excesses of from $10^3$ to $10^{10}$ being more preferred. These gross excesses are called for because the stability of the flooder-rare earth complexes is many orders of magnitude lower than the stability of the complex between the diamine and the rare earth metal.

The flooded complex is formed simply by adding the flooder to the already-formed rare earth chelate complex in solution. This is generally carried out immediately before measuring the fluorescence of the flooded complex. Although not known with certainty, it appears that the flooded complex that forms is a 1:1:1 molar ternary combination of species-linked diamine triacid:rare earth metal ion:flooder.

PREPARATIVE METHODS

The species-linked diamine triacids may be simply formed by contacting a species substance (which substance must contain at least one

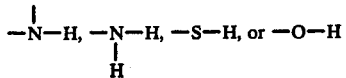

group) with a substantial molar excess of a diamine tetraacetic acid dianhydride of the formula shown in General Formula III in liquid phase in a polar aprotic liquid organic reaction medium. Useful reaction media include acetone, dimethylformamide (DMF), dimethylsulfoxide (DMSO) and HMPA, and the like. Mixtures of these materials may be used as well. When the reactive group on the species molecule is an amine, especially a primary amine, water may be used as solvent as may mixed solvents containing water.

This contacting is carried out under conditions that will permit the active group on the species molecule to react with one of the two anhydride groups on the diamine. In the case where the active group on the species molecule is an amine, the contacting will effect reaction at moderate conditions, such as at temperatures of from about 5° C. to about 100° C. with temperatures of from about 10° C. to about 75° C. being preferred. In the case where the active group on the species is a thiol or a hydroxyl, somewhat more strenuous conditions are generally employed such as temperatures from 25° C. to about 150° C. In this case, temperatures of from 35° C. to about 125° C. are preferred. This difference in reactivity may be utilized to effect selective reaction with amine groups and exclusion of reaction with thiols or hydroxyls, if such is of advantage. The reaction times employed, of course, are inversely dependent upon the temperature used. Generally, times of from about 0.5 hours to about two days are employed, with times of from one hour to about thirty-six hours being preferred. These times and temperatures are provided as guides. In certain situations, such as with extremely heat sensitive or heat insensitive targets, it may be of advantage to go outside of the exemplary ranges shown here. As a general rule, the use of lower temperatures within these ranges is to be preferred as they lead to better selectivity of the reaction between the anhydride and the species molecule.

It is essential that an excess of the dianhydride be employed. Dianhydride:species molecule ratios of at least 4:1 should be employed with ratios of from 5:1 to about 10:1 being preferred. The upper limit on this ratio is an arbitrary one based on a desire for economy. One may use amounts of anhydride greater than called for by this range and achieve good results. Such a mode of operation is considered to be within the scope of this invention but is also considered to be wasteful as the excess anhydride is destructively hydrolyzed in the workup which follows.

The dianhydrides employed herein are either art-known materials (see U.S. Pat. No. 3,497,535) or may be prepared from the corresponding diamine tetraacetic acids by the usual methods for preparing carboxylic diacid anhydrides such as by heating the tetraacid to 150° C. or thereabouts (say 80° C. to 180° C.) in the presence of a molar excess of acetic anhydride and a tertiary amine for a prolonged period such as for from 12 to 36 hours.

Following attachment of the species molecule to the dianhydride, the remaining anhydride group is hydrolyzed to the corresponding diacetic acid. This hydrolysis is easily carried out by admixing the coupling reaction mixture with an excess of water beyond the number of moles of anhydride to be hydrolyzed and heating. Suitable temperatures are in the range of from about 30° C. to about 125° C. Suitable times are from about one minute to about two hours. Preferred temperatures and times are in the ranges of 40° C. to 105° C. and two minutes to ninety minutes. Alternatively, other conditions known in the art for hydrolyzing carboxylic acid anhydrides to acids (e.g., acetic anhydride to acetic acid) may be employed.

The excess over stoichiometric of anhydride which is employed to form the species-linked triacid is separated from the species-linked material. This removal of the excess anhydride can take place either before or after hydrolysis of the anhydride to acid as is found to be most convenient. If the excess is not removed it will be available to react with metal ions and optional flooders if present and likely give rise to complexes which will interfere with the precise determination of the amount of species-linked diamine triacid. This separation of linked diamine from nonlinked can be effected by any method which will discriminate between the species-linked and nonlinked molecules. The two species differ in size so that chromatography techniques such as gel permeation chromatography, high pressure liquid chromatography, column chromatography, for example, using a silica gel substrate, or thin layer chromatography can be used. Membrane techniques including dialysis and ultrafiltration may also be used to effect this separation. In many cases, the linked material may differ from the nonlinked anhydride or acid by some physical property such as electrical charge or solubility. Such a property difference can also be used as a basis for separation, for example, by selective extraction or electrophoresis. Although we have employed and generally prefer the chromatographic separations, the exact method employed should be based on the actual materials and separation involved. The species-linked diamine triacid, freed of excess anhyride or acid is then formed into the metal complex.

The hydrolysis generates the desired species-linked diamine triacids of Formula I. These may be converted to the metal coordination compounds of Formula II by contacting the triacid with the desired metal ion. This contacting is generally carried out in solution. The amount of metal ion employed should be about one mole of ion per mole of triacid. The complex between the metal ion and the triacid is a strong one having large stability constants. This means that it is not required to employ gross excesses of metal ion to drive the complex-forming reaction and excesses of ion can in some cases interfere with the accuracy of later fluorescence measurements.

The metal complex-forming step is generally carried out in an aqueous reaction medium. The water-containing hydrolysis reaction medium can be very suitably employed, if desired. This means that the metal ions are generally added in the form of their water-soluble salts such as halides, nitrates, acetates, or the like, as is appropriate.

The addition of metal ion is suitably carried out at ambient conditions. Complex formation is not favored by highly elevated temperatures and significantly depressed temperatures are not seen to offer any advantages. A temperature range of from 5° C. to about 40° C. is generally preferred for convenience.

In the case of the rare earth metal ion complexes for fluorometric assay techniques it is often desired to add a "flooder" to the metal ion complex. This addition of flooder is usually carried out immediately prior to the measurement of the fluorescence. It is accomplished by adding the excess of flooder to the solution of the metal ion complex. This addition is carried out at moderate conditions as well, such as at a temperature of from 5° C. to 40° C.

SPECIES MOLECULES

Species molecules which may be covalently incorporated into the present species-linked diamine triacid materials and complexes of this invention are organic molecules selected from "target molecules" as these materials are described in above-noted U.S. Pat. Nos. 4,150,295 and 4,058,732, which are incorporated by reference, molecules essentially identical to "target molecules" and antibodies specific to "target molecule". These species molecules contain at least one of the groups primary amine, secondary amine, thiol, or hydroxyl. These active groups may be present intrinsically on the species molecule or they may be present on a "spacer" unit covalently linked to the species molecule. The spacer is of utility to minimize the possibility of interference between the diamine triacid group and the species molecule itself. Such interference could be detrimental in certain situations, such as when the species molecule must exhibit immune reactive properties or take part in some other substrate recognition step. The "spacer" may also be employed just to provide the needed amine, thiol or hydroxyl active groups. The term "species" includes materials with and without added spacers.

The use of spacer or "bridge" molecules to attach active molecules to nonactive groups, such as substrates has been developed in the fields of enzyme immobilization, chromatography, and the like. See, for example, U.S. Pat. No. 3,278,392 of Patchornik, U.S. Pat. No. 3,873,514 of Chu et al, and Wilchek, FEBS LETT, 33 (1), 70–72. These techniques, while not setting out the exact systems herein involved, do disclose a wide range of reagents and the advantages to be derived by the use of spacers.

Although this invention can be practiced with any species molecule which inherently, or through the use of a spacer, contains the required amine, thiol or hydroxyl group, it finds especially advantageous application with biologically active target molecules including therapeutic drugs, enzymes, hormones, peptides, macromolecules including proteins and lipids, haptens, antigens, and the like. Such molecules usually have at least one of the required active groups and often present difficult or even impossible analysis or detection problems because of the minute amounts in which they may be present in biological systems.

Examples of the species molecules thus can range from simple organic target molecules having the requisite functional groups, for example, lower alkanols—methanol, ethanol, butanol, hexanol, cyclohexanol, and the like; lower aromatic hydroxy compounds—phenol, 2,4-dinitrophenol and the cresols; lower alkyl and aromatic amines—ethylamine, diethylamine, butylamine, and isopropylamine; lower thiol—propane thiol and butane thiol; as well as targets up to the more complicated drug and biological molecules including the hormones thyroxine, triiodothyronine, human growth hormone gonadotropins, gastrointestinal hormones, insulin, and the like; therapeutic drugs such as digoxin, morphine, procain amide and the like; proteins, antibodies and the like. In the case of large molecules such as proteins and antibodies, there may be more than one (even a large number) of the requisite functional sites on each species molecule so that each species molecule may have more than one diamine triacid group covalently attached thereto. This list of possible species molecules is to demonstrate the wide range of targets that can be linked to the diamine triacids in accord with this invention. It is not intended to limit the scope of this invention.

ANALYSIS TECHNIQUES

As already described, the present invention enables the covalent attachment of complexes of metal ions to species molecules or to antibodies of species molecules. Detection of these metal ions by methods known to the art can be used to determine the presence or amount of the species molecules. As also already mentioned, if the metal ion incorporated is a radionucleotide, radioassay techniques can be used to determine the amount of species present. Alternatively, atomic absorption techniques can be used to measure the amount of metal and the amount of target thus determined.

In one preferred embodiment the metal is a rare earth and the resulting chelate is activated to fluorescence by a flooder or other means. The numerous techniques which have evolved in the radioimmunoassay field can in general be applied to fluorescence immunoassay. These include incubation techniques, competitive binding methods and separations of bound and free labeled targets as discussed, for example, in the texts Radioimmunoassay And Related Techniques by J. I. Thoreu et al, C. V. Mosby Co., St. Louis, Mo., (1978) and Radioimmunoassay in Clinical Biochemistry, Ed., C. A. Pasternak, Heyden, London, New York, Rheine, (1975).

The primary difference between radioimmunoassay and fluorescence immunoassay is in the final reading step. In the former case, radioactive disintegrations are counted, in the latter case, fluorescence is excited and measured.

Preferably, the time-gated fluorescence techniques disclosed in U.S. Pat. Nos. 4,150,295 and 4,058,732, both of Irwin Wieder, are employed as they permit substantially enhanced sensitivity to be achieved.

In the case of fluorescent antibodies tagged with the rare earth chelates of the present invention, they can be used to assay for free targets in the body fluids or in another preferred application they can be used to detect the presence of (or to quantify) specific kinds of biological cells or bacteria provided that these cells or bacteria have unique targets or groups of targets on their surface.

The invention will be further shown by the following Preparations and Examples. These are intended to exemplify the invention and are not to be construed as limiting its scope which is instead defined by the appended claims.

PREPARATION OF DIAMINE TETRAACETIC ACID DIANHYDRIDES

(a) Ethylenediamine Tetraacetic Acid Dianhydride

A mixture of ethylenediamine tetraacetic acid (EDTA) 364 g, 510 g of acetic anhydride and 600 g of pyridine are heated to 65° C. and there held for 24 hours. The mixture is then cooled and filtered in a glove box. The solid that is recovered is washed with diethyl ether and dried. It amounts to 96% of the theoretical weight of EDTA dianhydride. Elemental analysis confirms that this dianhydride is the product obtained.

(b) Propylenediamine Tetraacetic Acid Dianhydride

Following the procedure set forth in U.S. Pat. No. 3,660,388 of Dazzi, 92 g of 1,3 propylenediamine tetraacetic acid, 152 g of acetic anhydride and 113 g of pyridine are stirred for 24 hours at 65° C. The reaction product is evaporated to dryness under vacuum. The residue is recovered rinsed three times with diethyl ether and dried in a vacuum oven at 100° C. The dried product is the desired dianhydride.

(c) Phenylene 1,2-diamine Tetraacetic Acid Dianhydride

Following the procedure of Dazzi, 34 g of 1,3-phenylenediamine tetraacetic acid, 72 g of acetic anhydride and 39 of pyridine are stirred for 24 hours at 65° C. The mixture is cooled and filtered. The solid that is separated is washed with benzene and dried. It is the desired dianhydride.

EXAMPLE 1

A. Bonding Thyroxine to EDTA Dianhydride

A 100 ml flask is evacuated and flame dried followed by three cycles of evacuation and filling with dry argon. The flask is cooled and charged with 433 mg of EDTA dianhydride, which is produced as in the Preparations, and 300 mg of L-thyroxine sodium salt pentahydrate. This thyroid gland hormone is of fundamental importance being vital for normal growth and metabolism and may be obtained commercially. The mole ratio of dianhydride:hormone is 5:1. Addition of 10 ml of DMF gives a light yellow solution. The flask is foil covered and warmed to 55° C. for 20 hours. A spot test is used to show that all of the hormone has reacted with the dianhydride to give the product

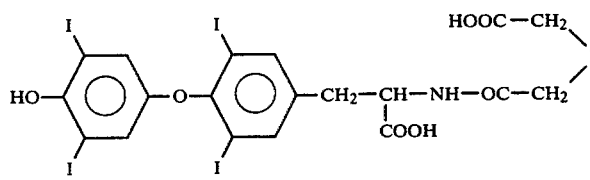

B. Hydrolyzing the Residual Anhydride

Product (A) is not isolated. Instead, 4 ml of distilled water is added to the flask and the heating is continued for an additional 1.5 hours. This causes the remaining anhydride group to hydrolyze yielding the thyroxine-linked ethylenediamine triacetic acid. The triacid and the EDTA that form are recovered as solids. The EDTA is recovered by filtration, washed with DMF and dried. The triacid passes through the filter and is recovered by evaporation of the filtrate.

C. Separating the EDTA from the Triacid

The crude product of Part (B) is eluted through a packed silica gel column using as eluent ethanol:water (95:5) followed by 80:20 95% aqueous ethanol:30% aqueous ammonia. The triacid elutes with the aqueous ethanol:aqueous ammonia and is collected as a pure compound by tlc. NMR, elemental analysis and IR scans verify that the recovered product is the desired thyroxine-linked triacid (C) as the ammonium salt in 59% yield.

D. Forming a Complex of C with a Rare Earth Ion

A known amount of the thyroxine-linked diamine triacetic acid recovered in part C is weighed out and dissolved in a few ml of 0.1 N NaOH. Within a few minutes, a stoichiometric quantity of a rare earth halide (specifically in this Example terbium chloride) is added and mixed to form a homogeneous solution containing the desired rare earth (terbium) ion/thyroxine-linked diamine triacetic acid 1:1 complex (D) and sodium chloride which is not an interfering factor.

E. Forming a Ternary Complex of D with a Flooder

An aliquot of the terbium complex of Part D is placed in 10 ml of water to give a concentration of about $10^{-8}$ molar. 5-sulfosalicylic acid in a concentration of $10^{-2}$ molar is added to form a terbium:thyroxine-linked diamine triacid:flooder complex. When excited at about 3300 Å, this complex exhibits a strong fluorescence which can be detected at 5450 Å. The application of this fluorescence property to the assay of thyroxine is shown hereafter.

EXAMPLE 2

The preparation of Example 1 is repeated with two changes. In place of terbium chloride in Step D, europium chloride is employed. Phenanthroline is used in place of 5-SSA as flooder. This results in the formation of the europium chelate and ternary complex corresponding to the terbium complexes formed in Example 1. The europium complex is fluorescent when used with a phenanthroline flooder and permits the determination of the amount of thyroxine present in solutions in accord with the method shown hereafter.

EXAMPLE 3

A. Bonding Cholesterol to EDTA Dianhydride Plus Hydrolysis

A 10 ml round bottomed flask is dried by flame heating and then filled with argon. It is then charged with 200 mg (0.52 mmol) of recrystallized cholesterol and 662 mg (2.59 mmol) of the dianhydride of Preparation a). The flask is left under vacuum for 45 minutes and then 3 ml of dried DMF is added and the mixture held at 90° C. for 36 hours. During this period the mixture remains essentially homogeneous and colorless. It is cooled to room temperature and 3 ml of deionized water is added with additional cooling. A precipitate forms and the heterogeneous mixture is stirred for 10 hours.

The mixture is diluted with 40 ml of diethyl ether-acetone (1:4) which results in additional precipitation. The mixture is filtered and the solid washed with 10 ml of the ether-acetone mixture. The filtrates are collected, evaporated and diluted with additional ether to cause more solid to form. This is collected and added to the previously collected solid. After drying, 322 mg (48% of theory) of the desired N-(ethanol-O-cholesterol-)ethylene-diaminetriacetic acid. Analysis by NMR and TLC shows that the product is very pure. Elemental analysis is consistent with the desired compound.

B. Forming Metal Ion Complex

The material of Part A (30 mg) is dissolved in 3 ml of 0.1 N NaOH. A rare earth metal ion (either terbium or dysprosium) is added in an approximately stoichiometric amount (1.00 to 1.05 moles per mole of the compound of Part A). This causes a rare earth metal ion complex of the material of Part A to form. This material, when promoted by the addition of an excess of a flooder exhibits fluorescence properties useful in fluoroassay methods. This addition of flooder is carried out as set forth in Example 1.

EXAMPLE 4

Coupling a Simple Alkanol

Isopropanol (1 mmol) is admixed with 10 ml of dried DMF in accord with the method of Example 3. Five mmols of the dianhydride of Preparation (a) is added and the mixture is held at 90° C. for 24 hours. This causes the alkanol's hydroxyl group to react with the anhydride and couple the alkanol in an ester configuration. This ester can be separated from the residual anhydride either before or after hydrolysis of the anhydride units. Complexes can be formed by admixing the ester with the desired metal ion.

EXAMPLE 5

Coupling a Simple Amine

The preparation of Example 4 is repeated with two changes. First, ethylamine is substituted for isopropanol on an equimolar basis. Second, the reaction conditions are less stressful, a temperature of 35° C. being employed. The ethylamine molecules add to the dianhydride in an amide configuration.

EXAMPLES 6-8

Coupling of Other Simple Groups

The coupling of Example 4 is repeated substituting phenol, ethylthiol, and diethylamine for the isopropanol employed in Example 4. In the case of diethylamine a lower temperature (35° C.) is employed as well. These repeats give rise to the coupled products based on each of the new starting materials. They may be further processed to form metal ion complexes, if desired.

EXAMPLE 9

Coupling an Amine in an Aqueous Environment

The coupling of Example 5 is repeated with two additional changes. In place of the DMF solvent, water is used and in place of the 35° C. for 24 hours, 30° C. and 36 hours is used. At these mild conditions the more active amine groups react and there is preferential attachment of the amines to the dianhydrides to form the desired triacids. This reaction is similar to the preferential reaction of an amine with acetic anhydride in an aqueous environment (see Caldwell, et al, *J.A.C.S.*, 64, 1695, (1942). This is a preferred method to couple triacids to proteins and antibodies.

EXAMPLE 10

A. Bonding Thyronine to PDTA Dianhydride

A dried flask is charged with 6 mmol of PDTA dianhydride, which is produced as in the Preparations, and 1 mmol of the essential amino acid thyronine, obtained from a commercial source. The mole ratio of dianhydride:thyronine is 6:1. DMF in the amount of 50 ml is added and the solution that forms is warmed to 35° C. and there maintained for 30 hours. The mixture is spot tested on a TLC plate and found to have no unreacted thyronine and to contain the desired thyronine-linked propylenediamine triacetic acid anhydride.

B. Hydrolyzing, Separating and Complexing

Following the general methods shown in Example 1, the anhydride of Part A. is hydrolyzed in situ and separated from the excess PDTA that forms by column chromatography. This yields the desired thyronine-linked triacetic acid. The solution of the desired triacid is divided into three equal parts. The first (estimated to contain about 0.2 mmoles of the triacid) is admixed with 1-2 mmoles of cobalt chloride as an aqueous solution. This gives rise to a cobalt chelate of the thyronine-linked triacetic acid. The second portion is contacted with 0.2 mmoles of terbium in the form of a solution of terbium bromide. This gives rise to a terbium chelate of the triacid. In accord with the method of Example 1, the flooder, 4-aminosalicylic acid, $1 \times 10^2$ mmoles, is added to form the 1:1:1 terbium/triacid/flooder complex. The third portion is carefully contacted with 1-2 mmoles of $In^{111}$ as its chloride. This gives rise to the $In^{111}$ complex of the thyronine-linked triacid.

EXAMPLE 11

The preparation of Example 5 is repeated with one change. Instead of EDTA dianhydride, cyclohexylene-1,2-diamine tetraacetic acid dianhydride is employed. This causes the ethylamine-linked triacetic acid to be formed. This compound,

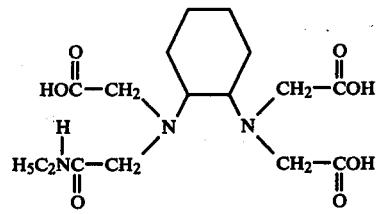

is contacted with europium ions to give rise to the europium complex which in turn is converted to a fluorescently active complex by addition of a $10^8$ molar excess of the flooder, potassium carbonate. This complex is detectable by fluorescence techniques.

Application of Target-linked Diamine Triacid Complexes to Assay of Target Molecules As a first step, the fact that fluorescence of a species-linked diamine triacid-rare earth metal ion complex is related to concentration of the complex is demonstrated. A serial dilution of a solution of the thyroxine-linked diamine triacetic acid complex with terbium (prepared as in Part D. of Example 1) is carried out with concentrations of the thyroxine of from $10^{-6}$ molar to $2.5 \times 10^{-11}$ molar. Flooder is added ($10^{-2}$ molar 5-sulfosalicylic acid). At pH 11.5, fluorescence of each of the samples is measured using a time-gated fluorimeter and measuring techniques set forth in Immunofluorescence and Related Staining Techniques, Knapp, et al, eds., 67–80, Elsevier/North Holland Biomedical Press, Amsterdam, 1978. The signals are plotted on log—log paper and seen to be linear over this range. The curve can be extrapolated to about $10^{-12}$ molar as a threshold detection limit. A threshold of detection is that concentration at which the fluorescent signal is just equal to the fluctuation in signals from a blank sample. The signals from a blank sample include photomultiplier dark noise and residual background signals from sample container, solvents, buffers, and the like. The fact that a linear plot is obtained shows that the concentration of a tagged species can be determined by measuring its fluorescence.

This finding is put to practical use, determining the concentration of thyroxine in unknown concentration samples in plasma. First, a standard curve is generated along the lines as in radioimmunoassay. A serial dilution of nonspecies-linked thyroxine is prepared in thyroxine-free plasma. Thyroxine-free plasma is made according to art-known techniques including denaturation of all thyroxine-bonding plasma proteins. The concentrations are 1, 2, 4, 8, and 16 µg/dl. pH is adjusted and a set amount of complex-linked thyroxine (D of Example 1) is added to each dilution along with a set amount of antibody to thyroxine. This mixture is incubated at conventional competitive binding conditions. The antibody-bound and free thyroxine are then separated using any of the art-known separation steps of ammonium sulfate precipitation, double antibody precipitation, polyethylene glycol precipitation, dextran-charcoal precipitation, column separation, or the like. The bound fraction is then suspended in buffer, flooder is added and fluorescence is measured using the time-gated process previously set forth. The observed fluorescence is plotted versus the concentration of the unlinked thyroxine in the standard samples. A curve is generated confirming that at larger concentrations of unlinked thyroxine the linked material is less able to compete for antibody sites and the observed fluorescence is lower. The curve that is generated is then used to determine the concentration of thyroxine in unknown samples.

Serum samples containing unknown amounts of thyroxine are assayed for total thyroxine. First they are acidified to denature any bonding proteins and free the thyroxine from any attachment. Then, after pH adjustment, they are treated with a standard amount of the thyroxine-linked diamine triacid metal complex of Part D., Example 1, and a standard amount of thyroxine antibody as was done in the generation of the standard curve. The mixture is incubated as above. Bound and unbound materials are separated. Flooder is added and the fluorescence is measured. The concentration of thyroxine in the unknown is then read from the standard curve based on the observed fluorescence.

Application of Antibody-linked Diamine Triacid Complexes to Assays

A. Assay for Antibody

In some cases the target molecule (molecule to be detected or measured) is an antibody. For example, it may be medically important to determine the spectrum of the immunoglobulin (IgE) antibodies in a human patient suffering from allergy. The patient may have IgE antibodies to various allergens and in different quantities, and for proper treatment it is crucial to know this distribution. To measure the amount of IgE antibodies in the blood or other body fluid the allergen in question is covalently coupled to a solid phase substrate using known art techniques and the substrate is exposed to the body fluid of the patient. After a suitable incubation period under suitable conditions the substrate is removed and washed. A representative amount of IgE antibody specific to the allergen on the solid substrate will now be present on the substrate, bound to the allergen. The substrate is now exposed to terbium chelated diamine triacid-linked antibody to human IgE; this anti IgE antibody is, in general, specific to all sub-classes of human IgE regardless of the allergen involved. After the second exposure, again under suitable conditions the solid substrate is again washed and exposed to a flooder such as sodium tungstate. The fluorescence is then measured preferably using a time-gated fluoromide as described above. Using known art procedures standard curves can be generated for each allergen with known amounts of IgE and the unknown amount of IgE in a human sample can thus be determined by comparison with a standard curve.

B. Assay for Cells or Bacteria

Cells or bacteria can have various molecular markers on their surfaces. These markers can, in some cases, be identified, isolated or purified and can be used to produce antibodies specific to the marker. Such antibodies, when linked to the diamine triacid metal complex of this invention can be used to identify certain cells or bacteria that have the markers on their surface. The cells or bacteria are exposed to the diamine triacid metal linked-antibodies and if the marker is present, a relatively high concentration of linked antibody is bound to the surface. These cells are then examined in a fluorescent microscope or fluorescent cell flow system and the fluorescent cells or bacteria are counted for a given volume, thus revealing their presence in a quantitative or qualitative fashion.

These are but two examples of the many possible assays that can be carried out using the species-linked diamine triacetic acid complexes of the present invention. Other equivalent procedures may be employed, as well.

What is claimed is:

1. A metal chelate for use in the fluorometric quantification of a biologically active organic species comprising an essentially 1:1 molar chelate complex of a rare earth metal ion capable of forming a fluorescent complex with a species-linked diamine triacetic acid having the structural formula:

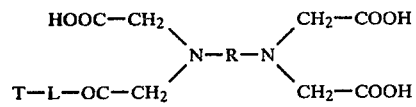

wherein R is a two to eight atom long covalent bridge selected from carbon-oxygen ether bridges, carbon-nitrogen secondary and tertiary amide bridges and carbon-carbon alkylene, cycloalkylene and arylene bridges, T is the biologically active organic species to be fluorometrically quantified, T being other than an aliphatic mono- or polyamine, or aliphatic mono- or polyol, but comprising at least one originally present or added primary amine, secondary amine, thiol or hydroxyl functional group, and L is said at least one functional group in deprotonated form covalently bonding T to the indicated carbonyl carbon of the diamine triacetic acid.

2. The metal chelate of claim 1 wherein the rare earth metal ion is selected from among ions of terbium, dysprosium, europium, samarium and neodimium.

3. The metal chelate of claim 1 wherein R is selected from two to eight atom long carbon-oxygen ether bridges and two to four carbon atom long alkylene bridges.

4. The metal chelate of claim 3 wherein the rare earth metal ion is selected from among ions of terbium, dysprosium, europium, samarium and neodimium.

5. The metal chelate of claim 1 wherein T is a therapeutic drug.

6. The metal chelate of claim 1 wherein T is an enzyme.

7. The metal chelate of claim 1 wherein T is a hormone.

8. The metal chelate of claim 1 wherein T is a macromolecular species.

9. The metal chelate of claim 1 wherein T is an antibody.

10. The metal chelate of claim 1 wherein T is a lipid.

11. The metal chelate of claim 1 wherein T is an antigen.

12. The metal chelate of claim 1 wherein T is a hapten.

13. The metal chelate of claim 1 wherein R is selected from the group consisting of ethylene, n-propylene, isopropylene, n-butylene, 1- and 2-methylpropylene, 1-propylethylene, 1-cyclohexylethylene, 1-phenylethylene, alkyl substituted 1-phenylethylenes and propylenes, 1-benzylethylene, 2-amidopropylene, cyclohexyl-1,2-ene, phenyl-1,3-ene, —CH$_2$—CH$_2$—O—CH$_2$—CH$_2$—, and —CH$_2$—CH$_2$—O—CH$_2$—CH$_2$—O—CH$_2$—CH$_2$—.

14. The metal chelate of claim 3 wherein the metal ion is selected from among the ions of europium and terbium.

15. The metal chelate of claim 14 wherein R is a two carbon atom long alkylene bridge.

16. The metal chelate of claim 15 wherein the metal ion is terbium ion.

17. An activated fluorescent rare earth metal ion chelate combination for use in the fluorometric quantification of a biologically active organic species comprising an essentially 1:1 molar chelate complex of a rare earth metal ion capable of forming a fluorescent complex with a species-linked diamine triacetic acid having the structural formula:

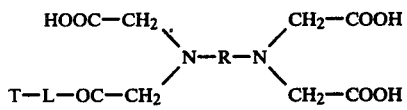

wherein R is a two to eight atom long covalent bridge selected from carbon-oxygen ether bridges, carbon-nitrogen secondary and tertiary amide bridges and carbon-carbon alkylene, cycloalkylene and arylene bridges, T is the biologically active organic species to be fluorometrically quantified, T being other than an aliphatic mono- or polyamine, or aliphatic mono- or polyol, but comprising at least one originally present or added primary amine, secondary amine, thiol or hydroxyl functional group, and L is said at least one functional group in deprotonated form covalently bonding T to the indicated carbonyl carbon of the diamine triacetic acid in combination with a fluorescent excitation efficiency promoter.

18. The activated fluorescent chelate combination of claim 17 wherein the rare earth metal ion is selected from among ions of terbium, dysprosium, europium, samarium and neodimium.

19. The activated fluorescent chelate combination of claim 17 wherein R is selected from two to eight atom long carbon-oxygen ether bridges and two to four carbon long alkylene bridges.

20. The activated fluorescent chelate complex of claim 19 wherein the rare earth metal ion is selected from among ions of terbium, dysprosium, europium, samarium and neodimium.

21. The activated fluorescent chelate complex of claim 17 wherein T is a therapeutic drug.

22. The activated fluorescent chelate complex of claim 17 wherein T is an enzyme.

23. The activated fluorescent chelate complex of claim 17 wherein T is a macromolecular species.

24. The activated fluorescent chelate complex of claim 17 wherein T is an antibody.

25. The activated fluorescent chelate complex of claim 17 wherein T is an antigen.

26. The activated fluorescent chelate complex of claim 17 wherein T is a lipid.

27. The activated fluorescent chelate complex of claim 17 wherein T is a hapten.

28. The activated fluorescent chelate complex of claim 17 wherein the fluorescent excitation efficiency promoter is a salicylate.

29. The activated fluorescent chelate complex of claim 27 wherein the metal ion is terbium ion, R is a two carbon atom long alkylene bridge and the fluorescent excitation efficiency promoter is 5-sulfosalicylic acid.

30. The process for preparing a fluorescent species-linked diamine triacetic acid which comprises the steps of a. contacting in liquid phase a biologically active organic species molecule having a functional group selected from

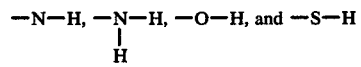

but being other than an aliphatic mono- or polyamine, or an aliphatic mono- or polyol with a molar excess of a diaminedianhydride of the formula

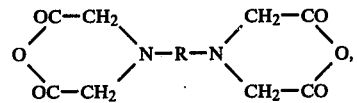

wherein R is a two to eight atom long covalent bridge selected from carbon-oxygen ether bridges, carbon-nitrogen secondary and tertiary amide bridges and carbon-carbon alkylene, cycloalkylene and arylene bridges, per mole of species molecule at a temperature of from about 5° C. to about 100° C. for from about 0.5 hours to about two days, b. hydrolyzing the remaining anhydride groups, c. recovering the species-linked diamine triacetic acid which is formed in step b, d. contacting the recovered species-linked diamine triacetic acid with a solution of a rare earth metal ion capable of forming a fluorescent complex with said triacetic acid and e. contacting said fluorescent complex with a substantial molar excess of a fluorescent excitation efficiency promoter.

* * * * *